US012067651B2

(12) United States Patent
Tang et al.

(10) Patent No.: US 12,067,651 B2
(45) Date of Patent: Aug. 20, 2024

(54) PROJECTION BASED DEEP LEARNING WITH FREQUENCY SPLITTING FOR COMPUTED TOMOGRAPHY

(71) Applicant: CANON MEDICAL SYSTEMS CORPORATION, Otawara (JP)

(72) Inventors: Qiulin Tang, Vernon Hills, IL (US); Ruoqiao Zhang, Vernon Hills, IL (US); Jian Zhou, Vernon Hills, IL (US); Zhou Yu, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 451 days.

(21) Appl. No.: 17/462,391

(22) Filed: Aug. 31, 2021

(65) Prior Publication Data
US 2023/0067596 A1   Mar. 2, 2023

(51) Int. Cl.
*G06T 11/00*   (2006.01)
*G06N 3/08*   (2023.01)
*G06T 7/00*   (2017.01)

(52) U.S. Cl.
CPC .............. *G06T 11/003* (2013.01); *G06N 3/08* (2013.01); *G06T 7/0012* (2013.01); *G06T 2207/20081* (2013.01); *G06T 2207/20084* (2013.01)

(58) Field of Classification Search
CPC ................ G06T 11/003; G06T 7/0012; G06T 2207/20081; G06T 2207/20084; G06T 2211/408; G06T 2211/441; G06T 11/005; G06T 11/006; G06N 3/08; G06N 3/0464; G06N 3/09; G06N 3/045; A61B 6/032; A61B 6/5205

USPC ......................................................... 382/131
See application file for complete search history.

(56) References Cited

U.S. PATENT DOCUMENTS

| 10,970,887 B2 | 4/2021 | Wang et al. |
| 2020/0196972 A1 | 6/2020 | Zhou et al. |
| 2021/0012541 A1 | 1/2021 | Lee et al. |
| 2021/0272336 A1* | 9/2021 | Yue ............................ G06T 7/11 |

FOREIGN PATENT DOCUMENTS

KR   2061967 B1   1/2020

OTHER PUBLICATIONS

Henri Der Sarkissian, Felix Lucka, Maureen van Eijnatten, Giulia Colacicco, Sophia Bethany Coban, Kees Joost Batenburg, "A cone-beam X-ray computed tomography data collection designed for machine learning." Published Oct. 22, 2019; https://www.nature.com/articles/s41597-019-0235-y.

* cited by examiner

*Primary Examiner* — Stephen P Coleman
(74) *Attorney, Agent, or Firm* — Oblon, McClelland, Maier & Neustadt, L.L.P.

(57) ABSTRACT

Data acquired from a scan of an object can be decomposed into frequency components. The frequency components can be input into a trained model to obtain processed frequency components. These processed frequency components can be composed and used to generate a final image. The trained model can be trained, independently or dependently, using frequency components covering the same frequencies as the to-be-processed frequency components. In addition, organ specific processing can be enabled by training the trained model using image and/or projection datasets of the specific organ.

18 Claims, 6 Drawing Sheets

PROJECTION BASED DEEP LEARNING WITH FREQUENCY SPLITTING FOR COMPUTED TOMOGRAPHY

BACKGROUND

In a computed tomography (CT) scan of an object, projection data containing information of the scanned object along the X-ray's path contains frequency components. These frequency components are often mixed and combined together. Therefore, higher frequency details, such as a small blood vessel or lesion, can become less visible and harder to detect. Furthermore, noise on the projection data may not be uniform due to different attenuations between different organs.

SUMMARY

In one embodiment, the present disclosure is related to a medical imaging system comprising: processing circuitry configured to obtain one or more frequency components of a real projection dataset acquired from scanning an object to be examined, the one or more frequency components of the real projection dataset each covering a predetermined frequency band; apply a trained model for improving image quality to the one or more frequency components of the real projection dataset to obtain one or more processed frequency components; and compose the one or more processed frequency components to obtain a set of processed projection data, wherein the trained model is generated by obtaining one or more frequency components of a lower quality projection dataset, the one or more frequency components of the lower quality projection dataset each covering a same predetermined frequency band as a frequency component from the one or more frequency components of the real projection dataset, obtaining one or more frequency components of a higher quality projection dataset, the one or more frequency components of the higher quality projection dataset each covering a same predetermined frequency band as a frequency component from the one or more frequency components of the real projection dataset, and generating the trained model by training one or more neural networks using the one or more frequency components of the lower quality projection dataset as input learning data and the one or more frequency components of the higher quality projection dataset as target learning data.

In one embodiment, the present disclosure is related to a medical imaging system comprising processing circuitry configured to extract a specific region from an image of an object reconstructed based on a projection dataset; obtain one or more frequency components of the specific region; apply a trained model for improving image quality to the one or more frequency components to obtain one or more processed frequency components; and generate a processed object image based on the one or more processed frequency components and the image of the object.

In one embodiment, the present disclosure is related to a processing method comprising: obtaining one or more frequency components of a real projection dataset acquired from scanning an object to be examined, the one or more frequency components of the real projection dataset each covering a predetermined frequency band; applying a trained model for improving image quality to the one or more frequency components of the real projection dataset to obtain one or more processed frequency components; and composing the one or more processed frequency components to obtain a set of processed projection data, wherein the trained model is generated by obtaining one or more frequency components of a lower quality projection dataset, the one or more frequency components of the lower quality projection dataset each covering a same predetermined frequency band as a frequency component from the one or more frequency components of the real projection dataset; obtaining one or more frequency components of a higher quality projection dataset, the one or more frequency components of the higher quality projection dataset each covering a same predetermined frequency band as a frequency component from the one or more frequency components of the real projection dataset; and generating the trained model by training one or more neural networks using the one or more frequency components of the lower quality projection dataset as input learning data and the one or more frequency components of the higher quality projection dataset as target learning data.

DETAILED DESCRIPTION

This disclosure is related to improving image quality by utilizing neural networks and frequency splitting. A projection dataset acquired from scanning an object can be decomposed into frequency components covering predetermined frequency ranges, and input into a trained model for producing processed frequency components. The processed frequency components can then be used to generate a higher quality image. The trained model can be trained, independently or dependently, using training data comprising high and low quality training pairs divided according to one or more frequency components covering the same predetermined frequency ranges. Further, specific regions of interest, such as the heart or lung, can be segmented out from an image and used for generating a model specifically trained to handle those regions.

In one embodiment, the present disclosure relates to a CT scanner. Of course, in an embodiment, any other system with medical image/projection data capable of generating frequency components can be used. However, for the sake of simplicity, discussions herein will focus a CT scanner.

Figure 1:
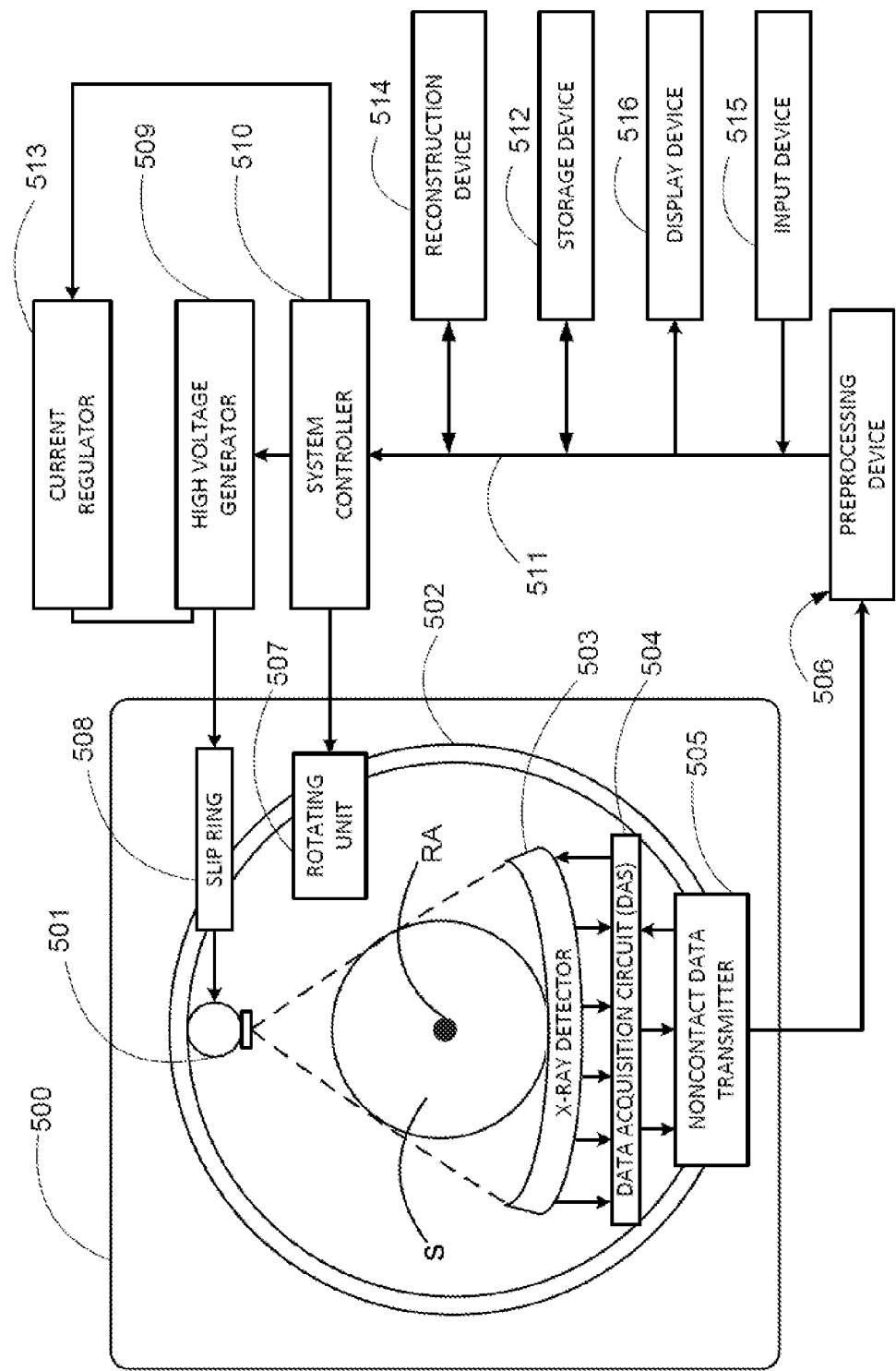
FIG. 1 is a block diagram of a CT scanner, according to one exemplary embodiment of the present disclosure.

FIG. 1 shows a schematic of an implementation of a CT scanner according to an embodiment of the disclosure. Referring to FIG. 1, a radiography gantry 500 is illustrated from a side view and further includes an X-ray tube 501, an annular frame 502, and a multi-row or two-dimensional-array-type X-ray detector 503. The X-ray tube 501 and X-ray detector 503 are diametrically mounted across an object OBJ on the annular frame 502, which is rotatably supported around a rotation axis RA (or an axis of rotation). A rotating unit 507 rotates the annular frame 502 at a high speed, such as 0.4 sec/rotation, while the subject S is being moved along the axis RA into or out of the illustrated page.

X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present disclosure can be applied to either type. The rotate/rotate type will be used as an example for purposes of clarity.

The CT apparatus further includes a high voltage generator 509 that generates a tube voltage applied to the X-ray tube 501 through a slip ring 508 so that the X-ray tube 501 generates X-rays (e.g. cone beam X-ray). The X-rays are emitted towards the subject S, whose cross sectional area is represented by a circle. For example, the X-ray tube 501 having an average X-ray energy during a first scan that is less than an average X-ray energy during a second scan. Thus, two or more scans can be obtained corresponding to different X-ray energies. The X-ray detector 503 is located at an opposite side from the X-ray tube 501 across the object OBJ for detecting the emitted X-rays that have transmitted through the object OBJ. The X-ray detector 503 further includes individual detector elements or units.

The CT apparatus further includes other devices for processing the detected signals from X-ray detector 503. A data acquisition circuit or a Data Acquisition System (DAS) 504 converts a signal output from the X-ray detector 503 for each channel into a voltage signal, amplifies the signal, and further converts the signal into a digital signal. The X-ray detector 503 and the DAS 504 are configured to handle a predetermined total number of projections per rotation (TPPR).

The above-described data is sent to a preprocessing device 506, which is housed in a console outside the radiography gantry 500 through a non-contact data transmitter 505. The preprocessing device 506 performs certain corrections, such as sensitivity correction on the raw data. A memory 512 stores the resultant data, which is also called projection data at a stage immediately before reconstruction processing. The memory 512 is connected to a system controller 510 through a data/control bus 511, together with a reconstruction device 514, input device 515, and display 516. The system controller 510 controls a current regulator 513 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 501 and the X-ray detector 503 are diametrically mounted on the annular frame 502 and are rotated around the object OBJ as the annular frame 502 is rotated about the rotation axis RA. In the fourth-generation geometry system, the detectors are fixedly placed around the patient and an X-ray tube rotates around the patient. In an alternative embodiment, the radiography gantry 500 has multiple detectors arranged on the annular frame 502, which is supported by a C-arm and a stand.

The memory 512 can store the measurement value representative of the irradiance of the X-rays at the X-ray detector unit 503. Further, the memory 512 can store a dedicated program for executing, for example, various steps of the methods and workflows discussed herein.

The reconstruction device 514 can execute various steps of the methods/workflows discussed herein. Further, reconstruction device 514 can execute pre-reconstruction processing image processing such as volume rendering processing and image difference processing as needed.

The pre-reconstruction processing of the projection data performed by the preprocessing device 506 can include correcting for detector calibrations, detector nonlinearities, and polar effects, for example.

Post-reconstruction processing performed by the reconstruction device 514 can include filtering and smoothing the image, volume rendering processing, and image difference processing as needed. The image reconstruction process can implement several of the steps of methods discussed herein in addition to various CT image reconstruction methods. The reconstruction device 514 can use the memory to store, e.g., projection data, reconstructed images, calibration data and parameters, and computer programs.

The reconstruction device 514 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 512 can be non-volatile, such as ROM, EPROM, EEPROM or FLASH memory. The memory 512 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 514 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 516. The display 516 can be an LCD display, CRT display, plasma display, OLED, LED or any other display known in the art.

The memory 512 can be a hard disk drive, CD-ROM drive, DVD drive, FLASH drive, RAM, ROM or any other electronic storage known in the art.

Figure 2:
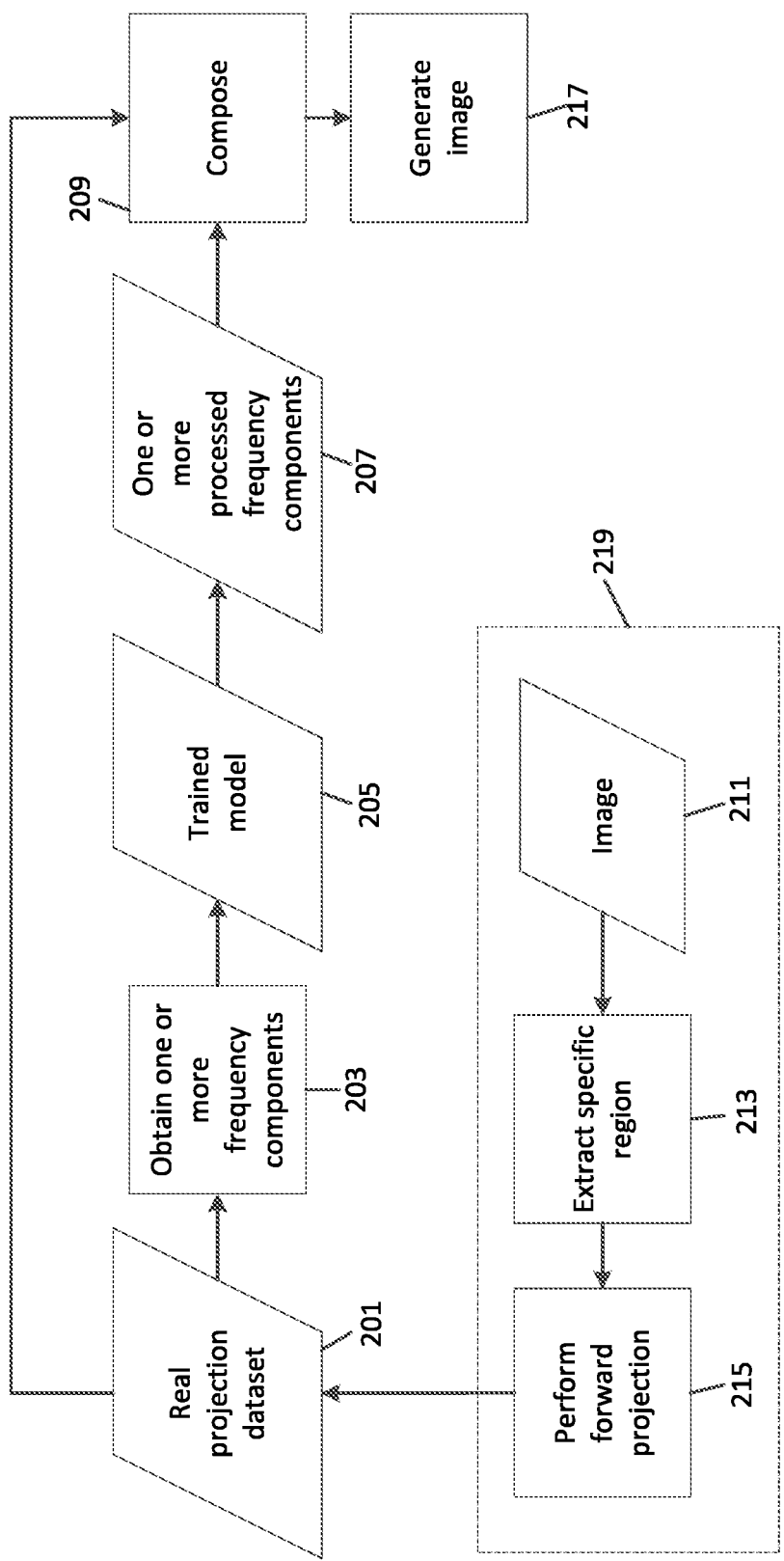
FIG. 2 illustrates a method for generating higher quality images by utilizing a trained model, according to one exemplary embodiment of the present disclosure.

FIG. 2 illustrates an overall framework of a method 200 for inferencing using a model trained according to the training techniques discussed herein.

A real projection dataset 201 is obtained. In one embodiment, the real projection dataset 201 is obtained from a scan of an object in a medical imaging scanner (e.g. radiography gantry 500). In one embodiment, as shown in sub-method 219, a scan of an object in a medical imaging scanner generates an image 211, where a specific region is extracted (e.g. heart, lungs, blood vessel) from the image 211 in step 213 and forward projected in step 215 to generate the real projection dataset 201. In other words, the real projection dataset can contain projection data from a scan of an entire region or a specific region. In the latter case, this can enable inferencing that is tailored towards specific organs. The real projection dataset 201 will include projection data having a range of frequencies.

In step 203, one or more frequency components are obtained from the real projection dataset 201. Each of the one or more frequency components contain projection data that is contained within a predetermined frequency range of the real projection dataset 201. In one embodiment, the predetermined frequency ranges covered by each of the frequency components, when combined together, span the entire frequency range of the real projection dataset 201. In one embodiment, the predetermined frequency ranges covered by each of the frequency components, when combined together, span only a subset of the entire frequency range of the real projection dataset 201.

As an example, if the real projection dataset 201 contains projection data with frequencies ranging from 20-50 kHz, in one scenario, two frequency components can be generated that span 20-50 kHz (e.g. one frequency component spanning 20-40 kHz, another frequency component spanning 40-50 kHz). In another scenario, two frequency components can be generated that span only portions of 20-50 kHz (e.g. one frequency component spanning 30-35 kHz, another frequency component spanning 40-45 kHz). In another scenario, one frequency component can be generated spanning only a portion of 20-50 kHz (e.g. one frequency component spanning 40-45 kHz). The number of frequency components and range of each frequency component can be adapted for any given scenario.

The frequency components can be obtained by applying filters (e.g. low-pass filter, band-pass filter, high-pass filter) to the real projection dataset 201. The range of frequencies covered by respective frequency components of the real projection dataset 201 can be determined based on the frequency components used to train the trained model 205. For example, if the trained model was trained using a set of training data whose frequency ranged was from 30-40 kHz, the frequency component obtained in step 203 can also contain projection data contained between 30-40 kHz of the real projection dataset 201.

The one or more frequency components obtained in step 203 are input into the trained model 205 to output one or more processed frequency components 207. The trained model 205 can include one or more neural networks combined together. The trained model 205 takes the one or more frequency components and outputs one or more processed frequency components 207. In one embodiment, the neural network is a deep convolutional neural network (DCNN). Additional discussion on how the trained model 205 is trained will be discussed later with reference to FIGS. 3, 4, 5, and 6.

In one embodiment, the trained model 205 includes one neural network trained to take each of the one or more frequency components obtained in step 203 as a channel input. In one embodiment, the trained model 205 includes a neural network specifically trained for each frequency range covered by the frequency components obtained in step 203 by training each neural network with training data also covering the same frequency range.

In step 209, a set of processed projection data is obtained by composing the one or more processed frequency components 207. This can be done by replacing all or portions of the real projection dataset 201 with the one or more processed frequency components 207. Projection data in the real projection dataset 201 with frequencies covered by the one or more processed frequency components 207 can be replaced.

For example, if the real projection dataset 201 contains projection data ranging from 20-50 kHz, a processed first frequency component contains projection data spanning frequency range 20-30 kHz, and a processed second frequency component contains projection data spanning frequency range 30-40 kHz, step 209 can include composing the projection data contained in the processed first frequency component, the processed second frequency component, and only the real projection dataset 201 contained within 40-50 kHz.

As another example, if the real projection dataset 201 contains projection data ranging from 20-50 kHz, a processed first frequency component contains projection data spanning frequency range 20-35 kHz, and a processed second frequency component contains projection data spanning frequency range 35-50 kHz, step 209 can include composing the processed first frequency component and the processed second frequency component (i.e. real projection dataset 201 is not used).

In step 217, the set of processed projection data output from step 209 is used to generate an image of the object. Any image reconstruction technique (e.g. analytical or iterative reconstruction) can be used in step 217. The generated image can also be displayed.

Figure 3:
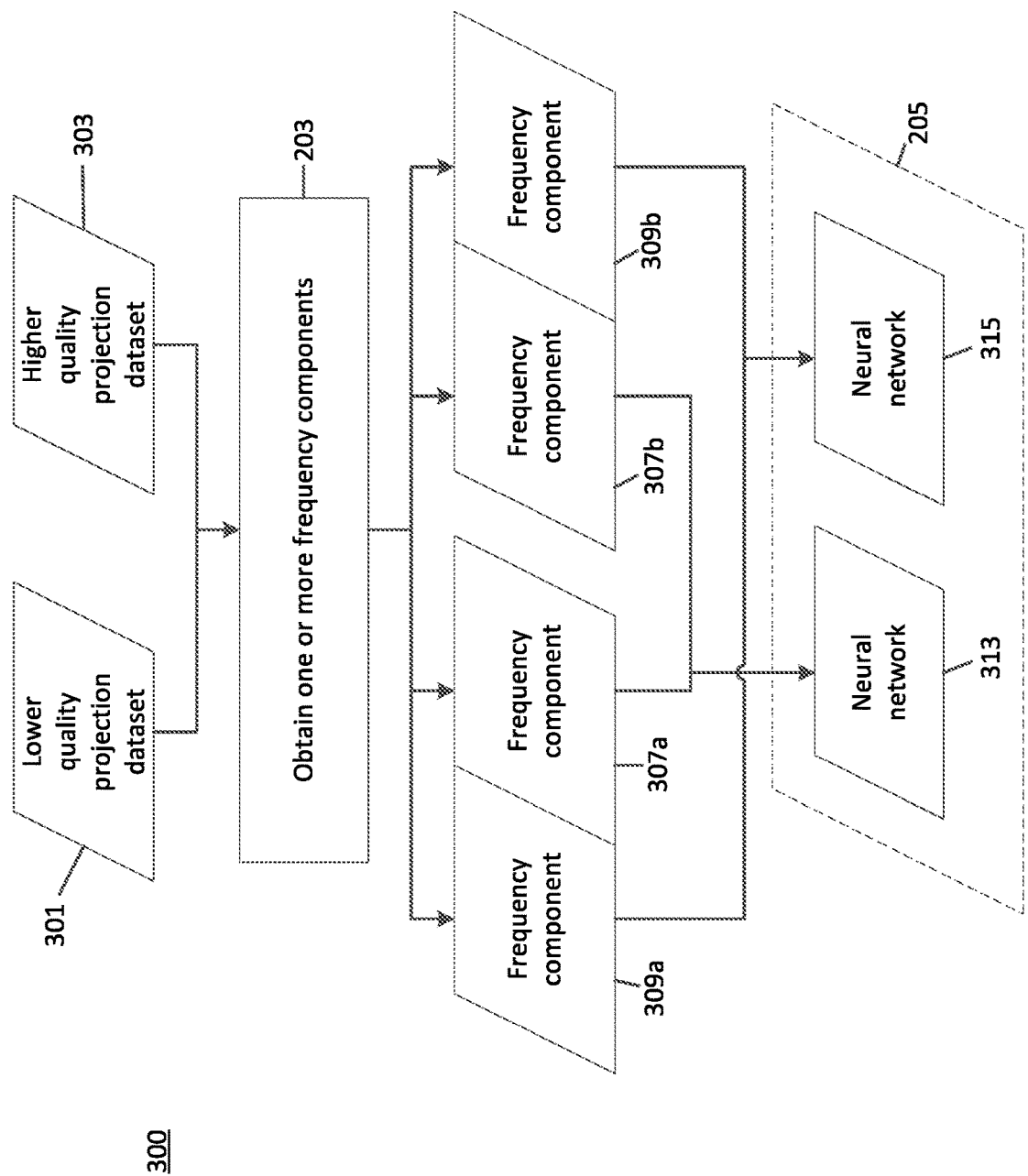
FIG. 3 illustrates a method for generating the trained model, according to one exemplary embodiment of the present disclosure.

FIG. 3 illustrates a method 300 of an exemplary technique for training a model to generate the trained model 205 used in method 200. First, a lower quality projection dataset 301 and higher quality projection dataset 303 are obtained. The lower quality projection dataset 301 and higher quality projection dataset 303 are projection datasets based on scans the same object, and can be obtained in a variety of ways. In an embodiment, the lower quality projection dataset 301 and higher quality projection dataset 303 can be obtained from a real scan of an object, a simulation of an object, or a combination thereof. In an embodiment, a superior system (e.g. less noisy, less scatter) can be used to scan and/or simulate an object to obtain the higher quality projection dataset 303, and an inferior system (e.g. more noisy, more scatter) can be used to scan and/or simulate the object to obtain the lower quality projection dataset 301. In an embodiment, the lower quality projection dataset 301 can be obtained from a real scan or simulation, and a quality enhancement technique (e.g. denoising, scatter removal) can be applied to generate the higher quality projection dataset 303 from the lower quality projection dataset 301. In an embodiment, the higher quality projection dataset 303 can be obtained from a real scan or simulation, and a degrading technique (e.g. add noise, add scatter) can be applied to generate the lower quality projection dataset 301 from the higher quality projection dataset 303.

Next, step 203 is performed to obtain one or more frequency components from the lower quality projection dataset 301 and the higher quality projection dataset 303. Step 203 performed in method 300 is the same as step 203 in method 200, meaning the same filters can be used; that way, the frequency ranges covered by the to-be-processed frequency component(s) from method 200 and the training data frequency component(s) from method 300 are identical.

In the exemplary illustration of FIG. 3, performing step 203 on the lower quality projection dataset 301 produces a frequency component 307a covering a first predetermined frequency range, and a frequency component 309a covering a second predetermined frequency range. Additionally, performing step 203 on the higher quality projection dataset 303 produces a frequency component 307b covering the same predetermined frequency range as frequency component 307a, and a frequency component 309b covering the same predetermined frequency range as frequency component 309a.

Of course the number of frequency components can be more or less than two depending on the specific application. Furthermore, the predetermined frequency range of the frequency component can vary according to the specific application. For example, imaging a smaller object (e.g. blood vessel) may have a frequency component covering larger frequency values than a larger object (e.g. lung) since the smaller an object is, the larger the frequency (i.e. smaller the wavelength) needs to be in order to image the object. As another example, processing an image with objects having a wide range of different sizes may have more frequency components than processing an image with objects having approximately similar sizes. Therefore, factor such as the size of a specific region of interest, total number of specific regions of interest, and variation in size of the specific regions of interest can be considered when predetermining the frequency component characteristics.

Returning back to method 300, the trained model 205 is trained. The frequency components of the lower quality projection dataset 301 are used in input learning data, and the frequency components of the higher quality projection dataset 303 are used as target learning data. Each of the neural networks 313, 315 are trained using frequency components where the input learning data and the target learning data cover a same predetermined frequency band. As shown in FIG. 3, neural network 313 is trained using frequency component 307a as input learning data and frequency component 307b as target learning data, while neural network 315 is separately trained using frequency component 309a as input learning data and frequency component 309b as target learning data. The training can take place until a predetermined stopping criteria has been met. The end result of method 300 is neural networks trained to optimize projection data contained in specific frequencies. During inferencing in method 200, neural networks 313, 315 can be used in series or parallel.

Figure 4:
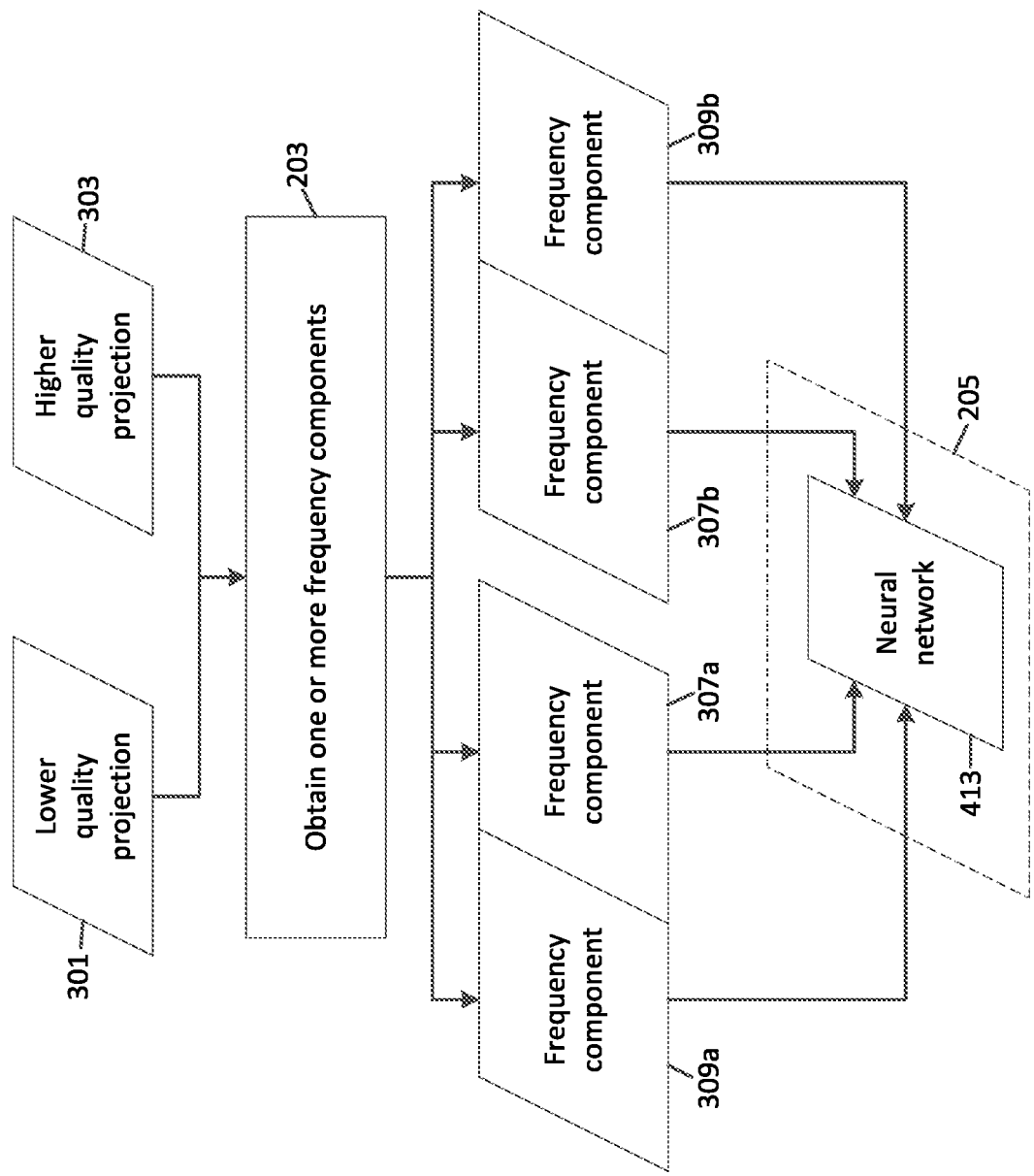
FIG. 4 illustrates a method for generating the trained model, according to one exemplary embodiment of the present disclosure.

FIG. 4 illustrates a method 400 of another technique to generate the trained model 205 that is similar method 300. However, rather than training multiple neural networks using independent training dataset pairs, a single neural network is trained using multiple channel inputs/outputs. As shown in FIG. 4, the neural network 413 is trained using (1) frequency component 307a and frequency component 309a as input learning data, and (2) frequency component 307b and frequency component 309b as output learning data. The neural network 413 is trained until a predetermined stopping a criterion has been met, thereby generating the trained model 205.

In one embodiment, desired regions can be extracted and used in the frequency splitting to generate the frequency components for use in training. By training using projection data from a specific region (e.g. lungs, heart, head), the trained model can be tailored to generate inferences of specific regions with efficiency and accuracy.

Figure 5:
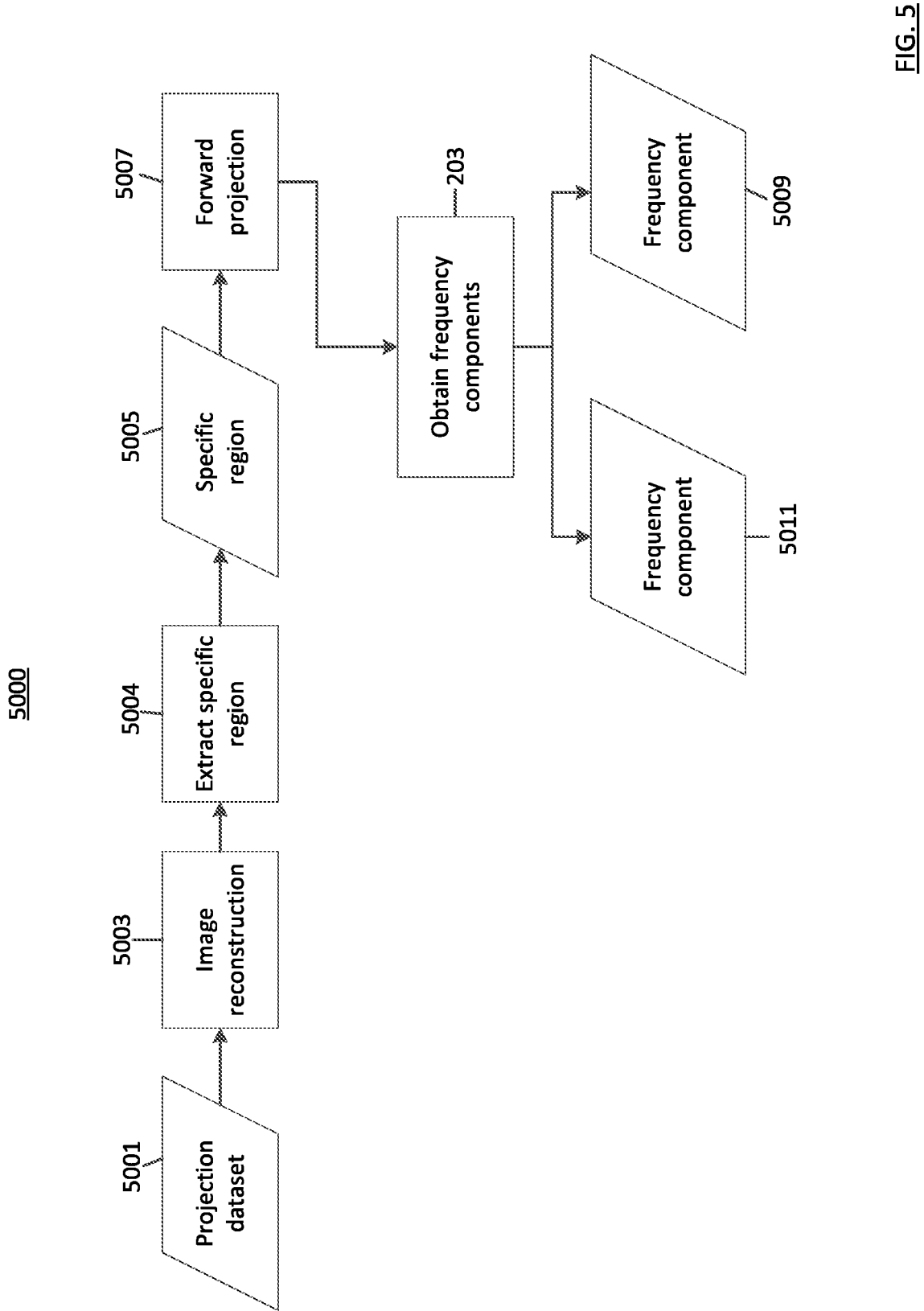
FIG. 5 illustrates a method for generating training data for a specific region, according to one exemplary embodiment of the present disclosure.

FIG. 5 illustrates a method 5000 of an exemplary embodiment for generating training data. A projection dataset 5001 is acquired, which can be acquired from a real scan or simulated scan of an object. This projection dataset 5001 can be a high or low quality projection dataset.

Next, image reconstruction is performed in step 5003 to transform the projection dataset 5001 into an image. Any image reconstruction technique, such as filtered backprojection, can be used.

The image output from step 5003 is then used in step 5004 to extract a specific region. For example, if the desired region to be extracted is the heart, only the image of the heart is extracted (i.e. kept), and the rest of the image (e.g. head, arms) is discarded. The specific region extracted in step 5004 is the same region as that extracted in step 213 of method 200 (e.g. heart of one patient and heart of a different patient). The output of step 5004 is an image of the specific region 5005 that was extracted.

In step 5007, the specific region 5007 is forward projected to generate projection data of the specific region. This projection data is then used to obtain one or more frequency components in step 203. Details of step 203 were discussed previously with respect to method 300 and 400. The output of step 203 is one or more frequency components, which can be used as either input learning data or target learning data. In the illustration of FIG. 5, the output of step 203 is frequency component 5009 and frequency component 5011.

The same process discussed with respect to FIG. 5 can be repeated to generate the other half of the training data. For example, if the projection dataset 5001 was used as a lower quality projection dataset, the same process can be repeated where the projection dataset is now a higher quality projection dataset.

Figure 6:
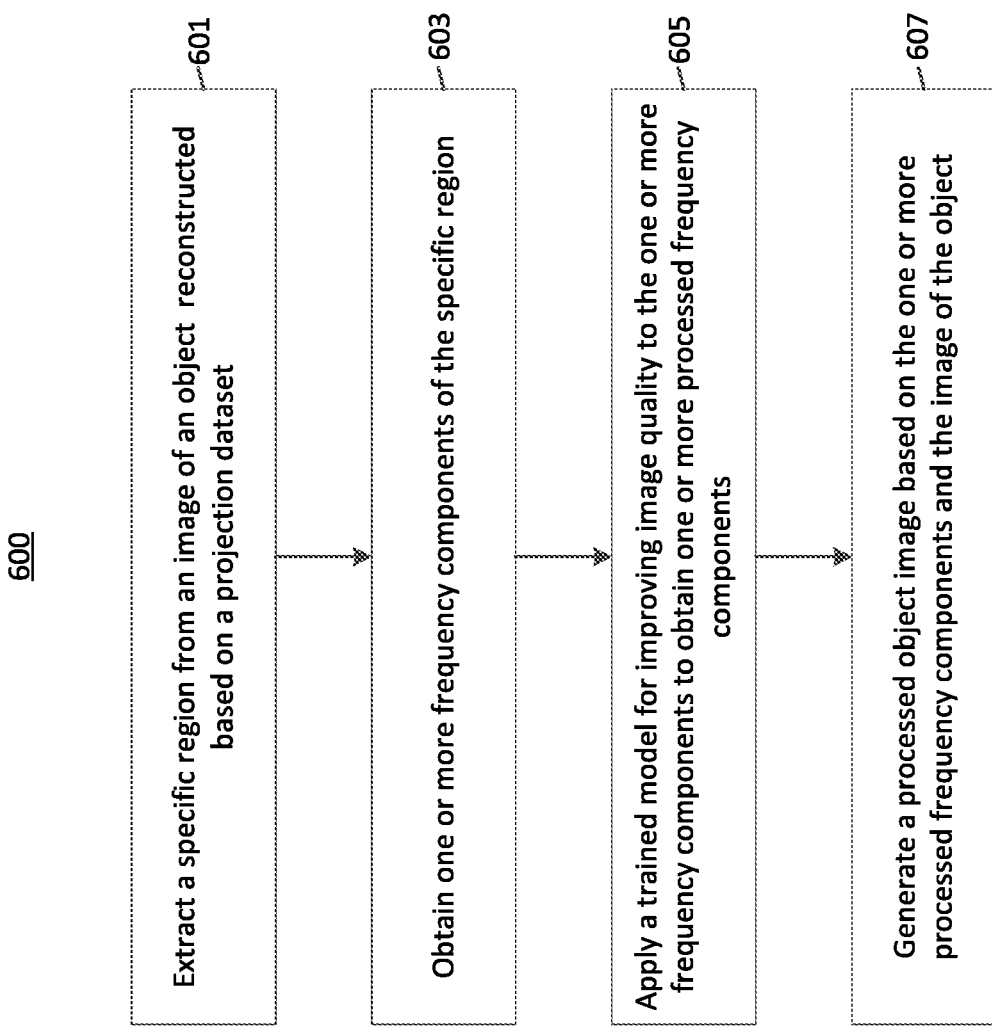
FIG. 6 illustrates a method for generating higher quality images by utilizing a trained model, according to one exemplary embodiment of the present disclosure.

In an embodiment, processing can be done in the image domain. FIG. 6 shows a flowchart of a method 600 according to one exemplary embodiment. Step 601 is extracting a specific region from an image of the object reconstructed based on a projection dataset. For example, the specific region can be an image of a heart extracted from a full body image reconstructed based on a full body scan of a patient using a CT scanner.

Step 603 is obtaining one or more frequency components of the specific region. The frequency range covered by each of the one or more frequency components should be the same as the frequency range covered by the training data. Note that in step 603, the one or more frequency components are obtained from an image rather than a projection dataset.

Step 605 is applying a trained model for improving image quality to the one or more frequency components to obtain one or more processed frequency components. The trained model can be trained using similar techniques to those discussed previously, except now the training is in the image domain. For example, instead of obtaining frequency components from lower and higher quality projection datasets, they can be obtained from lower and higher quality image datasets of the specific region.

Step 607 is generating a processed object image based on the one or more processed frequency components and the image of the object. For example, if the original image of the object contained a heart and lung, and the processed frequency components represent a higher quality image of the heart, the processed object image can include the original lung and the higher quality image of the heart.

The method and system described herein can be implemented in a number of technologies but generally relate to processing circuitry for performing the techniques described herein. In one embodiment, the processing circuitry is implemented as one of or as a combination of: an application specific integrated circuit (ASIC), a field programmable gate array (FPGA), a generic array of logic (GAL), a programmable array of logic (PAL), circuitry for allowing one-time programmability of logic gates (e.g., using fuses) or reprogrammable logic gates. Furthermore, the processing circuitry can include a computer processor and having embedded and/or external non-volatile computer readable memory (e.g., RAM, SRAM, FRAM, PROM, EPROM, and/or EEPROM) that stores computer instructions (binary executable instructions and/or interpreted computer instructions) for controlling the computer processor to perform the processes described herein. The computer processor circuitry may implement a single processor or multiprocessors, each supporting a single thread or multiple threads and each having a single core or multiple cores. In an embodiment in which neural networks are used, the processing circuitry used to train the artificial neural network need not be the same as the processing circuitry used to implement the trained artificial neural network that performs the denoising described herein. For example, processor circuitry and memory may be used to produce a trained artificial neural network (e.g., as defined by its interconnections and weights), and an FPGA may be used to implement the trained artificial neural network. Moreover, the training and use of a trained artificial neural network may use a serial implementation or a parallel implementation for increased performance (e.g., by implementing the trained neural network on a parallel processor architecture such as a graphics processor architecture).

In the preceding description, specific details have been set forth, such as a particular method and system for improving medical image quality through the use of neural networks. It should be understood, however, that techniques herein may be practiced in other embodiments that depart from these specific details, and that such details are for purposes of explanation and not limitation. Embodiments disclosed herein have been described with reference to the accompanying drawings. Similarly, for purposes of explanation, specific numbers, materials, and configurations have been set forth in order to provide a thorough understanding. Nevertheless, embodiments may be practiced without such specific details. Components having substantially the same functional constructions are denoted by like reference characters, and thus any redundant descriptions may be omitted.

Various techniques have been described as multiple discrete operations to assist in understanding the various embodiments. The order of description should not be construed as to imply that these operations are necessarily order dependent. Indeed, these operations need not be performed in the order of presentation. Operations described may be performed in a different order than the described embodiment. Various additional operations may be performed and/or described operations may be omitted in additional embodiments.

Those skilled in the art will also understand that there can be many variations made to the operations of the techniques explained above while still achieving the same objectives of the invention. Such variations are intended to be covered by the scope of this disclosure. As such, the foregoing descriptions of embodiments of the invention are not intended to be limiting. Rather, any limitations to embodiments of the invention are presented in the claims.

Embodiments of the present disclosure may also be as set forth in the following parentheticals.

(1) A medical imaging system comprising: processing circuitry configured to obtain one or more frequency components of a real projection dataset acquired from scanning an object to be examined, the one or more frequency components of the real projection dataset each covering a predetermined frequency band; apply a trained model for improving image quality to the one or more frequency components of the real projection dataset to obtain one or more processed frequency components; and compose the one or more processed frequency components to obtain a set of processed projection data, wherein the trained model is generated by obtaining one or more frequency components of a lower quality projection dataset, the one or more frequency components of the lower quality projection dataset each covering a same predetermined frequency band as a frequency component from the one or more frequency components of the real projection dataset, obtaining one or more frequency components of a higher quality projection dataset, the one or more frequency components of the higher quality projection dataset each covering a same predetermined frequency band as a frequency component from the one or more frequency components of the real projection dataset, and generating the trained model by training one or more neural networks using the one or more frequency components of the lower quality projection dataset as input learning data and the one or more frequency components of the higher quality projection dataset as target learning data.

(2) The system of (1), wherein the processing circuitry is further configured to extract a specific region from an image of the object reconstructed based on the scanning; and perform forward projection on the specific region to obtain a partial projection dataset, wherein the partial projection dataset is used as the real projection dataset.

(3) The system of any (1) to (2), wherein for each neural network in the one or more neural networks, the neural network is trained using (1) a frequency component from the one or more frequency components of the higher quality projection dataset, and (2) a corresponding frequency component from the one or more frequency components of the lower quality projection dataset, the frequency component from the one or more frequency components of the higher quality projection dataset and the corresponding frequency component from the one or more frequency components of the lower quality projection dataset covering identical frequencies.

(4) The system of any (1) to (3), wherein the one or more neural networks is one neural network, the one neural network trained using each of the one or more frequency components of the lower quality projection dataset as channel inputs to be used as the input learning data, and each of the one or more frequency components of the higher quality projection dataset as channel outputs to be used as the target learning data.

(5) The system of any (1) to (4), wherein the lower quality projection dataset is generated by extracting a specific region from a second image of a second object reconstructed based on a second projection dataset; and performing forward projection on the specific region to obtain a partial projection dataset, wherein the partial projection dataset is used as the lower quality projection dataset.

(6) The system of any (1) to (5), wherein the higher quality projection dataset is generated by extracting a specific region from a second image of a second object reconstructed based on a second projection dataset; and performing forward projection on the specific region to obtain a partial projection dataset, wherein the partial projection dataset is used as the higher quality projection dataset.

(7) The system of any (1) to (6), wherein the processing circuitry is further configured to reconstruct an image based on the set of processed projection data.

(8) The system of any (1) to (7), wherein a range of the predetermined frequency band for each of the one or more frequency components of the real projection dataset are based on a size of a specific region in the object to be examined.

(9) The system of any (1) to (8), wherein the medical imaging system is a CT scanner.

(10) A medical imaging system comprising processing circuitry configured to extract a specific region from an image of an object reconstructed based on a projection dataset; obtain one or more frequency components of the specific region; apply a trained model for improving image quality to the one or more frequency components to obtain one or more processed frequency components; and generate a processed object image based on the one or more processed frequency components and the image of the object.

(11) The system of (10), wherein the medical imaging system is a CT scanner.

(12) A processing method comprising: obtaining one or more frequency components of a real projection dataset acquired from scanning an object to be examined, the one or more frequency components of the real projection dataset each covering a predetermined frequency band; applying a trained model for improving image quality to the one or more frequency components of the real projection dataset to obtain one or more processed frequency components; and composing the one or more processed frequency components to obtain a set of processed projection data, wherein the trained model is generated by obtaining one or more frequency components of a lower quality projection dataset, the one or more frequency components of the lower quality projection dataset each covering a same predetermined frequency band as a frequency component from the one or more frequency components of the real projection dataset; obtaining one or more frequency components of a higher quality projection dataset, the one or more frequency components of the higher quality projection dataset each covering a same predetermined frequency band as a frequency component from the one or more frequency components of the real projection dataset; and generating the trained model by training one or more neural networks using the one or more frequency components of the lower quality projection dataset as input learning data and the one or more frequency components of the higher quality projection dataset as target learning data.

(13) The method of (12), further comprising: extracting a specific region from an image of the object reconstructed based on the scanning; and; performing forward projection on the specific region to obtain a partial projection dataset, wherein the partial projection dataset is used as the real projection dataset.

(14) The method of any (12) to (13), wherein for each neural network in the one or more neural networks, the neural network is trained using (1) a frequency component from the one or more frequency components of the higher quality projection dataset, and (2) a corresponding frequency component from the one or more frequency components of the lower quality projection dataset, the frequency component from the one or more frequency components of the higher quality projection dataset and the corresponding frequency component from the one or more frequency components of the lower quality projection dataset covering identical frequencies.

(15) The method of any (12) to (14), wherein the one or more neural networks is one neural network, the one neural network trained using each of the one or more frequency components of the lower quality projection dataset as channel inputs to be used as the input learning data, and each of the one or more frequency components of the higher quality projection dataset as channel outputs to be used as the target learning data.

(16) The method of any (12) to (15), further comprising extracting a specific region from a second image of a second object based on a second projection dataset; and performing forward projection on the specific region of the second object to obtain a partial projection dataset, wherein the partial projection dataset is used as the lower quality projection dataset.

(17) The method of any (12) to (16), further comprising extracting a specific region from a second image of a second object based on a second projection dataset; and performing forward projection on the specific region to obtain a partial projection dataset, wherein the partial projection dataset is used as the higher quality projection dataset.

(18) The method of any (12) to (17), further comprising reconstructing an image based on the set of processed projection data.

(19) The method of any (12) to (18), wherein a range of the predetermined frequency band for each of the one or more frequency components of the real projection dataset are based a size of a specific region in the object to be examined.

(20) The method of any (12) to (19), wherein the scanning is performed by a CT scanner.

The invention claimed is:

1. A medical imaging system, comprising:
processing circuitry configured to
obtain one or more frequency components of a real projection dataset acquired from scanning an object to be examined, the one or more frequency components of the real projection dataset each covering a predetermined frequency band;
apply, to a trained model for improving image quality, the one or more frequency components of the real projection dataset to obtain one or more processed frequency components; and
compose the one or more processed frequency components to obtain a set of processed projection data, wherein the trained model is generated by
obtaining one or more frequency components of a lower quality projection dataset, the one or more frequency components of the lower quality projection dataset each covering a same predetermined frequency band as a frequency component from the one or more frequency components of the real projection dataset,
obtaining one or more frequency components of a higher quality projection dataset, the one or more frequency components of the higher quality projection dataset each covering a same predetermined frequency band as a frequency component from the one or more frequency components of the real projection dataset, and
generating the trained model by training one or more neural networks using the one or more frequency components of the lower quality projection dataset as input learning data and the one or more frequency components of the higher quality projection dataset as target learning data.

2. The system of claim 1, wherein the processing circuitry is further configured to
extract a specific region from an image of the object reconstructed based on the scanning; and
perform forward projection on the specific region to obtain a partial projection dataset, wherein the partial projection dataset is used as the real projection dataset.

3. The system of claim 1, wherein for each neural network in the one or more neural networks, and the processing circuitry is further configured to train the neural network using
(1) a frequency component from the one or more frequency components of the higher quality projection dataset, and
(2) a corresponding frequency component from the one or more frequency components of the lower quality projection dataset,
the frequency component from the one or more frequency components of the higher quality projection dataset and the corresponding frequency component from the one or more frequency components of the lower quality projection dataset covering identical frequencies.

4. The system of claim 1, wherein the one or more neural networks is one neural network, and the processing circuitry is further configured to train the one neural network using each of the one or more frequency components of the lower quality projection dataset as channel inputs for the input learning data, and each of the one or more frequency components of the higher quality projection dataset as channel outputs for the target learning data.

5. The system of claim 1, wherein the processing circuitry is further configured to generate the lower quality projection dataset by:
extracting a specific region from a second image of a second object reconstructed based on a second projection dataset; and
performing forward projection on the specific region to obtain a partial projection dataset, wherein the partial projection dataset is used as the lower quality projection dataset.

6. The system of claim 1, wherein the processing circuitry is further configured to generate the higher quality projection dataset by:
extracting a specific region from a second image of a second object reconstructed based on a second projection dataset; and
performing forward projection on the specific region to obtain a partial projection dataset, wherein the partial projection dataset is used as the higher quality projection dataset.

7. The system of claim 1, wherein the processing circuitry is further configured to reconstruct an image based on the set of processed projection data.

8. The system of claim 1, wherein a range of the predetermined frequency band for each of the one or more frequency components of the real projection dataset is based on a size of a specific region in the object to be examined.

9. The system of claim 1, wherein the medical imaging system is a CT scanner.

10. A processing method, comprising:
obtaining one or more frequency components of a real projection dataset acquired from scanning an object to be examined, the one or more frequency components of the real projection dataset each covering a predetermined frequency band;
applying, to a trained model for improving image quality, the one or more frequency components of the real projection dataset to obtain one or more processed frequency components; and
composing the one or more processed frequency components to obtain a set of processed projection data, wherein the trained model is generated by
obtaining one or more frequency components of a lower quality projection dataset, the one or more frequency components of the lower quality projection dataset each covering a same predetermined frequency band as a frequency component from the one or more frequency components of the real projection dataset;
obtaining one or more frequency components of a higher quality projection dataset, the one or more frequency components of the higher quality projection dataset each covering a same predetermined frequency band as a frequency component from the one or more frequency components of the real projection dataset; and
generating the trained model by training one or more neural networks using the one or more frequency components of the lower quality projection dataset as input learning data and the one or more frequency components of the higher quality projection dataset as target learning data.

11. The method of claim 10, further comprising:
extracting a specific region from an image of the object reconstructed based on the scanning; and
performing forward projection on the specific region to obtain a partial projection dataset, wherein the partial projection dataset is used as the real projection dataset.

12. The method of claim 10, further comprising, for each neural network in the one or more neural networks, training the neural network using
(1) a frequency component from the one or more frequency components of the higher quality projection dataset, and
(2) a corresponding frequency component from the one or more frequency components of the lower quality projection dataset,
the frequency component from the one or more frequency components of the higher quality projection dataset and the corresponding frequency component from the one or more frequency components of the lower quality projection dataset covering identical frequencies.

13. The method of claim 10, wherein the one or more neural networks is one neural network, and the method further comprises training the one neural network using each of the one or more frequency components of the lower quality projection dataset as channel inputs for the input learning data, and each of the one or more frequency components of the higher quality projection dataset as channel outputs for the target learning data.

14. The method of claim 10, further comprising:
extracting a specific region from a second image of a second object based on a second projection dataset; and
performing forward projection on the specific region of the second object to obtain a partial projection dataset, wherein the partial projection dataset is used as the lower quality projection dataset.

15. The method of claim 10, further comprising:
extracting a specific region from a second image of a second object based on a second projection dataset; and
performing forward projection on the specific region to obtain a partial projection dataset, wherein the partial projection dataset is used as the higher quality projection dataset.

16. The method of claim 10, further comprising reconstructing an image based on the set of processed projection data.

17. The method of claim 10, wherein a range of the predetermined frequency band for each of the one or more frequency components of the real projection dataset is based a size of a specific region in the object to be examined.

18. The method of claim 10, wherein the scanning is performed by a CT scanner.

* * * * *